United States Patent [19]

Sanders et al.

[11] Patent Number: 4,959,217

[45] Date of Patent: Sep. 25, 1990

[54] DELAYED/SUSTAINED RELEASE OF MACROMOLECULES

[75] Inventors: Lynda M. Sanders, Palo Alto, Calif.; Abraham Domb, Brookline, Mass.

[73] Assignee: Syntex (U.S.A.) Inc., Palo Alto, Calif.

[21] Appl. No.: 866,042

[22] Filed: May 22, 1986

[51] Int. Cl.$^5$ .................................................. A61K 9/24
[52] U.S. Cl. ................................ 424/473; 424/486; 424/487; 424/425; 424/427; 424/433; 424/436
[58] Field of Search ................ 514/800; 424/473, 425, 424/427, 486, 433, 436, 487

[56] References Cited

U.S. PATENT DOCUMENTS

| | | | |
|---|---|---|---|
| 3,416,530 | 12/1968 | Ness | 128/260 |
| 3,551,556 | 12/1970 | Kliment | 424/21 |
| 3,618,604 | 11/1971 | Ness | 128/260 |
| 3,710,795 | 1/1973 | Higuchi | 128/260 |
| 3,828,777 | 8/1974 | Ness | 128/260 |
| 3,832,252 | 8/1974 | Higuchi | 156/86 |
| 3,854,480 | 12/1974 | Zaffaroni | 128/260 |
| 3,903,880 | 9/1975 | Higuchi | 128/130 |
| 3,946,106 | 3/1976 | Chien et al. | 424/427 X |
| 3,948,254 | 4/1976 | Zaffaroni | 128/127 |
| 3,993,072 | 11/1976 | Zaffaroni | 128/260 |
| 4,010,125 | 3/1977 | Schally et al. | 260/8 |
| 4,014,335 | 3/1977 | Arnold | 424/427 X |
| 4,024,121 | 5/1977 | Schally et al. | 514/800 X |
| 4,052,505 | 10/1977 | Higuchi | 424/14 |
| 4,069,307 | 1/1978 | Higuchi et al. | 424/22 |
| 4,127,127 | 11/1978 | Wong | 128/260 |
| 4,190,642 | 2/1980 | Gale et al. | 424/19 |
| 4,298,002 | 11/1981 | Ronel et al. | 424/424 X |
| 4,309,996 | 1/1982 | Theeuwes | 424/424 X |
| 4,391,797 | 7/1983 | Folkman et al. | 424/427 X |
| 4,402,695 | 9/1983 | Wong | 604/892 |
| 4,432,964 | 2/1984 | Shell et al. | 424/427 |
| 4,452,775 | 6/1984 | Kent | 424/425 |
| 4,475,916 | 10/1984 | Himmelstein | 424/427 X |
| 4,548,990 | 10/1985 | Mueller et al. | 525/123 |
| 4,613,330 | 9/1986 | Michelson | 424/424 |
| 4,667,014 | 5/1987 | Nestor, Jr. et al. | 514/800 X |
| 4,668,506 | 5/1987 | Bawa | 424/427 X |

FOREIGN PATENT DOCUMENTS

| | | |
|---|---|---|
| 0046136 | 2/1982 | European Pat. Off. . |
| 0092918 | 11/1983 | European Pat. Off. . |
| 0121331 | 10/1984 | European Pat. Off. . |
| 0141584 | 5/1985 | European Pat. Off. . |
| 1420885 | 1/1976 | United Kingdom ................ 424/427 |

OTHER PUBLICATIONS

Davis, *Proc. Nat. Acad. Sci. U.S.A.*, 71 (8): 3120–3123 (1974).
Shell, et al., *Ann. Opthalmal.*, 6 (10): 1037–1045 (1974).
Abrahms, et al., *J. Biomed. Mater. Res.*, 9: 355–366 (1975).
Lee, et al., *J. Colloid & Interface Sci.*, 51 (2): 225–231 (1975).
Olanoff, et al., *J. Pharm. Sci.*, 68 (9): 1147–1155 (1979).
Cardinal, et al., *Controlled Release of Bioactive Materials:* 123–133 (Richard Baker, ed., Academic Press, 1980).
Kim, et al., *ACS Symposium Series,* 127 (20): 347–359 (1980).
Lee, et al., *J. Membrane Sci.,* 7:293–303 (1980).
Tuttle, et al., *J. Membrane Sci.,* 7: 351–358 (1980).
Wisniewski, et al., *J. Membrane Sci.,* 6: 299–308 (1980).
Cardinal, et al., *AIChE Symposium Series,* 77: 52–61 (1981).
Olanoff, et al., *A.I.Ch.E. Symposium Series,* 206, 77: 21–27 (1981).
Wood, et al., *J. Pharm. Pharmacol.*, 34: 1–4 (1982).
Mack et al., *Topics in Pharm. Sci.,* 265–275 (Elsevier Science Publishers, 1983).
Wood, et al., *Drug Dev. Ind. Pharm.,* 9: 93–101 (1983).
Graham, et al., *Biomaterials (Guildford, Engl.),* 5 (1): 27–36 (1984).
Ishiara, et al., *Polymer J.,* 16, (8): 647–651 (1984).
Migliaresi, et al., *J. Biomed. Mater. Res.,* 18: 137–146 (1984).

*Primary Examiner*—Thurman K. Page
*Attorney, Agent, or Firm*—David A. Lowin; John A. Dhuey

[57] ABSTRACT

This invention concerns novel, delayed/sustained release devices and compositions, including methods of their manufacture and use. The compositions include macromolecules, particularly polypeptide pharmaceuticals, and an initially partially-hydrated, non-biodegradable, hydrogel rate-limiting membrane.

48 Claims, 4 Drawing Sheets

DELAYED/SUSTAINED RELEASE OF MACROMOLECULES

BACKGROUND OF THE INVENTION

1. Field of the Invention

This invention relates to the controlled release of macromolecules, particularly hydrophilic macromolecules. More specifically, it relates to the delayed/sustained release of pharmaceutical compositions, particularly polypeptides such as luteinizing hormone-releasing hormones ("LH-RH"), mammalian growth hormones, mammalian growth hormone-releasing hormones, polypeptides having thymosin-like activity, and the analogs thereof. Specifically, the invention relates to drug delivery devices having an initially partially-hydrated, non-biodegradable hydrogel rate-limiting membrane. These delivery systems, which may include ocular inserts and implantable devices, delay the release of macromolecules until after placement in a delivery environment, and then facilitate a sustained, preferably zero-order release thereof.

2. Background Information

The sustained release of active agents is known to be of value. Particularly in the administration of certain pharmaceuticals, long-term drug delivery has been shown to be most effective in that constant serum levels are obtained and patient compliance is improved. Delaying the release of such agents is also desirable in that an immediate release upon placement in the delivery environment can result in unacceptably high initial concentrations of a drug at the situs of implantation or use.

The examination of synthetic hydrogels for potential biomedical applications (including potential use in certain drug delivery devices) has given rise to various theories regarding mechanisms of diffusion. Lee, Jhon and Andrade have proposed that there are three classes of water in hydrogels, using polyHEMA (hydroxyethyl methacrylate) as their model [*Nature of Water in Synthetic Hydrogels, J. Colloid & Interface Sci.*, 51 (2): 225-231 (1975)]. The first 20% of hydrogel water content, called "Z water", was said to be bound to the polymer matrix. The next 10-12% of water content, called interfacial or "Y water", is partially affected by the polymer matrix. Any additional water imbibed by the gel is relatively unaffected by the polymer matrix; it is called bulk or "X water".

The Lee, et al. model was expanded upon by Kim, Cardinal, Wisniewski and Zentner [*Solute Permeation Through Hydrogel Membranes: Hydrophilic vs. Hydrophobic Solutes, ACS Symposium Series (Water in Polymers)*, 127 (20): 347-359 (1980)]. They concluded that the diffusion coefficients for hydrophilic solutes through hydrogel membranes depends on molecular size and water content; permeation in pure polyHEMA and in polyHEMA crosslinked with a low mole percent of ethyleneglycoldimethacrylate ("EGDMA") was via the pore mechanism, i.e., through the bulk-type water. Hydrophobic solutes were said to diffuse via both pore and partition mechanisms, i.e., respectively through the bulk-type water, and through the interfacial-type and bound-type water. Neither article, however, included any suggestion as to how such diffusion characteristics might be applied to the design of a delayed/sustained delivery device.

Wood, Attwood and Collett have described a model for diffusion of the small hydrophobic molecule salicylic acid (the solute) in hydrogels [*The influence of gel formulation on the diffusion of salicylic acid in polyHEMA hydrogels, J. Pharm. Pharmacol.*, 34: 1-4 (1982)]. Radioactively labelled salicylic acid was added to a HEMA monomer solution and polymerized in situ. The water contents of the resulting gels were measured. Diffusion was measured by quantifying migration of the solute to a gel placed in contact with the sample gels. It was concluded that diffusion occurred primarily through the polymer's pores via the hydrating liquid at higher levels of hydration (more than 31%). At hydration levels below 31%, diffusion was said to occur by dissolution of the solute within the polymer segments; crosslinker concentration did not have any significant effect on diffusion. This was correlated to a change in pore size proportional with percent hydration. Wood, et al. did not, however, offer any teaching as to the effects of percent hydration on delayed/sustained release of hydrophilic macromolecular compositions. For another treatment of the interaction of pore size and diffusion, see Wisniewski and Kim [*J. Membrane Sci.*, 6: 299-308 (1980)].

Controlled and sustained release compositions are known in the art for progesterone. [See Mack, et al., *Topics in Pharm. Sci.*, pp. 265-275 (1983).] A variety of devices have been described, for example, in the article by Cardinal, Kim, Song, Lee and Kim [*Controlled Release Drug Delivery Systems from Hydrogels: Progesterone Release from Monolithic, Reservoir, Combined Reservoir-Monolithic and Monolithic Devices with Rate Controlling Barriers, AIChE Symposium Series*, 77: 52-61 (1981)].

Microporous membranes (some including hydrogels) have been used as rate-limiting barriers for such devices, including implants, ocular inserts, coated intrauterine devices and the like, e.g., as described in U.S. Pat. Nos. 3,416,530 (to Ness—entitled "Eyeball Medication Dispensing Tablet"); 3,551,556 (to Kliment, et al.—entitled "Carriers for Biologically Active Substances"); 3,618,604 (to Ness—entitled "Ocular Insert"); 3,828,777 (to Ness—entitled "Microporous Ocular Device"); and 4,548,990 (to Mueller, et al.—entitled "Crosslinked, Porous Polymers for Controlled Drug Delivery").

In U.S. Pat. No. 3,993,072 (to Zaffaroni—entitled "Microporous Drug Delivery Device") and in its parent patents 3,948,254 (entitled "Novel Drug Delivery Device") and 3,854,380 (entitled "Drug-Delivery System"), drug delivery systems are disclosed including a solid inner matrix containing a drug and surrounded by a wall formed of a polymeric membrane (the '072 and '254 patents call for a microporous membrane, the pores of which contain a drug-release-rate-controlling medium).

Some sustained release devices have been described for the delivery of hydrophilic macromolecules, such as polypeptides. For example, European Patent Application Publication No. 0,092,918 (to Churchill, et al.—entitled "Continuous Release Formulations") describes the continuous release of, e.g., luteinizing hormone-releasing hormone, growth hormones and growth hormone releasing factor, from a hydrophobic/hydrophilic non-crosslinked copolymer in which the hydrophobic component is biodegradable and the hydrophilic component may or may not be biodegradable. The composition is described as being capable of absorbing water to form a hydrogel when placed in an aqueous, physiological-type environment.

These prior devices depend on the relationship between the drug's diffusivity in the reservoir, its diffusivity in the delivery environment, and its diffusivity through the membrane. In other words, the diffusivity through the membrane has to be the least of the three, in order for the membrane to serve as a rate-limiting barrier. They all generally rely on Fick's First Law of Diffusion, in which the flux of a solute through a membrane is related to the area and thickness of the membrane, the permeability coefficient of the solute for that membrane material, and the concentration of the solute.

In attempts to apply the prior art relating to hydrogel-based delivery devices to macromolecules, it was discovered that none of the prior devices solve the following problems:

(i) Such devices release macromolecules as soon as the device is in place.

(ii) Such devices cause an initial spike of drug release in the delivery environment.

(iii) Such devices are difficult to handle during implantation, due to their flexibility.

(iv) Non-hydrated (or xerogel) devices are relatively fragile as compared to hydrated hydrogel devices, in that their rate controlling membranes are quite brittle and tend to chip or crack when handled (e.g., during implantation), potentially destroying the sealed reservoir environment required for zero-order release.

The present invention solves all of the foregoing problems through the use of an initially partially-hydrated, non-biodegradable, hydrogel rate-limiting membrane surrounding a suitable carrier and a macromolecular composition.

SUMMARY OF THE INVENTION

Devices are disclosed for the delayed/sustained release of macromolecules having a molecular weight greater than about 1,000, including the administration of macromolecular pharmaceutical compositions. The devices include a carrier, e.g., a pharmaceutically acceptable carrier, saturated with, and containing excess solid of, the macromolecular composition. An initially partially-hydrated, non-biodegradable, hydrogel rate-limiting membrane formed of a homopolymer or a copolymer (a "[co]polymer") material surrounds the carrier. The devices of the invention are provided with the membrane being only partially hydrated; i.e., sufficiently hydrated to be non-brittle, but hydrated only to such an extent that the devices remain structurally manipulable and are substantially non-permeable to the macromolecular composition prior to placement in the delivery environment.

The devices useful in the invention include surgical implants, suppositories, vaginal inserts and ocular inserts of the reservoir-, monolithic-, monolithic reservoir-, and monolithic with rate controlling barrier layer-types. They all have in common the use of a hydrogel rate-limiting membrane to control the release of the active agent(s) contained therein; in the monolithic-type device, the carrier also serves as the rate-limiting membrane.

In one aspect, the invention covers a pharmaceutical formulation designed for delayed/sustained release of an effective amount of a drug over an extended period of time, wherein the formulation comprises at least one hormonally active, water-soluble polypeptide in an effective amount greater then a conventional single dose, suspended in a carrier (e.g., silicone oil or a [co]-polymer) and surrounded with a membrane (e.g., initially partially hydrated, crosslinked or non-crosslinked [co]polymers including hydroxyethyl methacrylate ("HEMA"), glycerol methacrylate ("GMA"), and methyl methacrylate ("MMA").

In another aspect, the invention covers a method of making a device designed for delayed/sustained release of an effective amount of a macromolecular composition, wherein the method includes initially partially hydrating the device's membrane to a water content at which it is substantially non-permeable to the macromolecular composition and also structurally manipulable.

In still another aspect, the invention covers a method for the delivery of a macromolecular composition by introducing into a delivery environment an initially partially hydrated device as described above.

DETAILED DESCRIPTION OF THE INVENTION

The Devices

Figure 1:
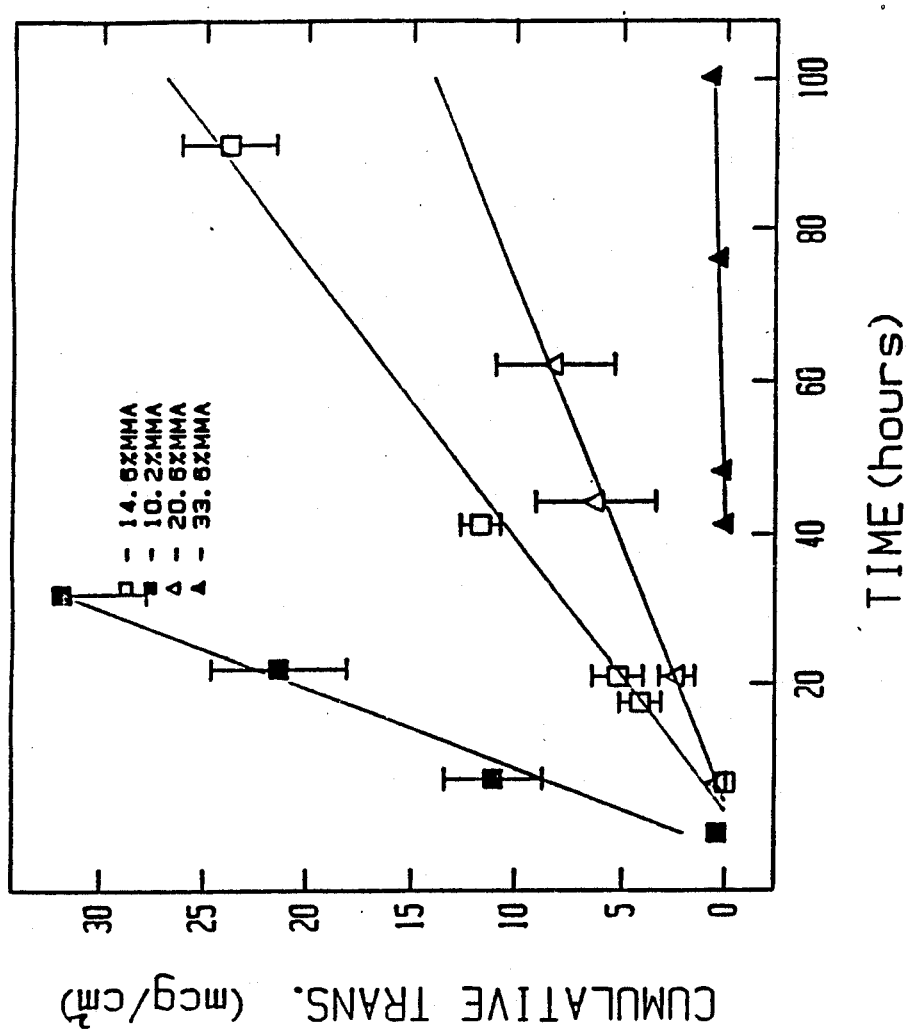
FIG. 1 is a graph showing cumulative transport vs. time, for the macromolecular composition nafarelin acetate through HEMA/MMA cast copolymer rate-limiting membranes, prepared in accordance with the present invention.

The devices of the present invention will be described in connection with their most preferred use, i.e., the delayed/sustained release of pharmaceutical agents to animals, including: humans; domestic animals such as bovines, porcines, sheep, goats and the like; pets such as cats, dogs, rabbits and the like; and domestic fowl such as chickens, turkeys, geese, ducks and the like. Delayed/sustained release is defined as delaying the release of an active agent until after placement in a delivery environment, followed by a sustained, preferably zero-order release thereof at a later time. Other applications of the present invention include controlled (e.g., delayed/sustained) delivery in industrial, agricultural and domestic settings.

The devices of the invention include surgical implants, suppositories, vaginal inserts and ocular inserts of the reservoir-, monolithic-, monolithic reservoir-, and monolithic with rate controlling barrier layer-types. The surgical implants are applied by implantation subcutaneously in an animal. The ocular inserts are applied by placement in the cul-de-sac of the conjunctiva between the sclera of the eyeball and the lower eyelid of an animal. The suppositories and vaginal inserts are applied by insertion into the appropriate body cavity. All of the devices have in common the use of a hydrogel rate-limiting membrane to control the release of the active agent(s) contained therein; in the monolithic-type device, the carrier also serves as the rate-limiting membrane.

These devices are all prepared for use in the invention based in part on techniques that are known in the art. For example, initial preparation of known devices is described in the article by Cardinal, Kim, Song, Lee and Kim, supra., and, e.g., in U.S. Pat. Nos. 3,416,530; 3,618,604, 3,828,777 and 3,948,254.

A hydrogel is typically a [co]polymer material, characterized by its ability to imbibe a liquid. The monomer or comonomers (the "[co]monomers") (with or without crosslinkers) that form the [co]polymer can be polymerized by exposure to an initiator and/or a source of polymerizing energy (e.g., heat or irradiation) to ultimately form a structurally well-defined, dry (i.e., non-hydrated) [co]polymer, commonly referred to as a xerogel. The xerogel comprises a system of polymer molecules oriented with respect to each other in such a manner that there exists a network of spaces (called interstitial spaces) between them. The xerogel is very hydrophilic, and thus absorbs liquids. Liquid is attracted by the hydrophilicity of certain portions of the [co]monomer molecules, and becomes disposed in the free volume (or interstitial spaces), causing the matrix to expand by stretching the [co]polymer molecules apart. As the xerogel absorbs such liquids it becomes hydrated, and is then referred to as a hydrogel. Polymerization can also take place in an aqueous solution, to give a partially or fully hydrated hydrogel rather than a xerogel. The degree to which any [co]polymer will ultimately hydrate depends largely on the [co]monomers from which it is made, including the extent to which it is crosslinked.

It has surprisingly been discovered that the release of macromolecules can be delayed, and then controlled by regulating the extent to which a hydrogel rate-limiting membrane is hydrated at various times during its use. By providing a device in the partially hydrated state, the free volume in the hydrogel matrix can be selected to be too small for the macromolecules to diffuse through. Later, upon placement of the device into a delivery environment, e.g., implantation or insertion in an animal, the partially hydrated hydrogel absorbs fluid from the environment and swells until it becomes fully hydrated; the matrix, therefore, enlarges and ultimately allows diffusion of the macromolecules through it. The hydrogel [co]polymer is also selected, depending upon the macromolecular composition to be released, to reach a maximum level of hydration (or "equilibrium water content") in the chosen environment, to thus limit the amount of swelling and thereby establish a delivery rate and duration.

The delayed/sustained release devices of the present invention are "structurally manipulable", i.e., flexible enough to not be brittle (and crack upon handling), yet rigid enough to maintain their shape during handling (to facilitate insertion into the delivery environment). This advantage is also obtained by providing the devices in an initially partially hydrated state.

Device Design

Manufacture of the delayed/sustained release devices of the invention requires that several factors be considered. The release profile (i.e., delay time, release rate and duration) and environment (e.g., the eye or subcutaneous tissue) must be determined. The materials must be selected, as must the type, shape and size of the device.

Once a [co]polymeric material for the rate-limiting membrane has been identified, the diffusivity of the macromolecular composition through it must be measured. The hydration profile of the rate limiting membrane for a given macromolecular composition may be determined by preparing a film of the selected [co]polymer and subjecting it to a diffusion study, using a two compartment vertical glass cell (as is well known in the art).

The diffusion coefficient, and the water content at which diffusion begins (i.e., below which substantially no diffusion occurs—hereinafter "% $H_d$") are determined. A series of membranes is prepared from various crosslinked and non-crosslinked [co]polymers. The membranes are then hydrated to their capacity and their equilibrium water contents are measured. The fully hydrated membranes are placed in the two-compartment, vertical glass cells to measure and plot the diffusion of the macromolecular composition through the membrane materials at the various equilibrium water contents. The equilibrium water content of the most hydrated membrane through which no diffusion is detected (i.e., none of the macromolecular composition diffuses into the receptor cell) is the % $H_d$ for the system being tested. This is best done by plotting a curve of the permeability vs. equilibrium water content.

The permeability results (diffusion coefficients) are obtained according to Fick's First Law of Diffusion, by use of the equation:

$$\frac{dQ}{dt} = \frac{APC_d}{l}$$

wherein:
   dQ/dt is the flux through the membrane material (μg/hr); it is measured as the slope of the linear part of the curve of cumulative transport versus time;
   A is the area of the membrane ($cm^2$);
   P is the membrane's permeability coefficient ($cm^2$/hr), or $DK_d$, wherein:
      D is the diffusivity in the membrane ($cm^2$/hr), and
      $K_d$ is the partition coefficient for the membrane/donor solution;
   l is the membrane thickness as measured at the end of the experiment (cm); and
   $C_d$ is the concentration of the donor solution (μg/$cm^3$).

The release delay profile is then determined. Another series of membranes is prepared, again varying the amounts of crosslinker and [co]monomers. These membranes are then hydrated, but only partially, i.e., to a water content less than or equal to % $H_d$. This can be accomplished by exposing the membrane to a hydrating liquid, removing the membrane from the liquid after a time calculated to result in the desired water content, and blotting it to arrest hydration. Alternatively a xerogel membrane can be fully hydrated by immersion in a hydrating liquid for a time sufficient for it to imbibe to its capacity (equilibrium water content), and then be subsequently dried (e.g., in a dessicator or an oven) to the desired water content (determined by measuring the membrane's weight). The partially hydrated membranes are placed in two-compartment vertical glass cells to measure and plot the diffusion of the macromolecular composition through the membranes versus time. Buffer solutions for the donor and receptor cells may be selected to contact the partially hydrated membranes and further hydrate them at approximately the same rate at which they will hydrate in the delivery environment (e.g., saline solution to predict release delay time in the environment of the eye). The time between commencement of the diffusion study (i.e., addition of the macromolecular composition to the donor cell) and the detection of a pharmaceutically effective concentration of the macromolecular composition in the receptor cell is the release delay time for that combination of [co]polymer and initial percent hydration.

In order to determine the physical dimensions of the device, the total amount of drug to be delivered must be determined. This is the product of the desired daily dosage and the duration of delivery. Particularly for zero order release, excess drug must be provided in order to maintain a saturated solution of the drug in the carrier with the presence of excess solid. Thus, the total amount of drug would be that amount required to saturate the carrier plus excess solid equal to the total amount of drug to be delivered.

Next, the minimum volume of the drug and carrier may need to be determined. This can be done by calculating volume based on a prior determination of the drug's solubility in the carrier, or more practically, by actually making the saturated solution and measuring its volume. This will be the minimum volume required for the reservoir.

In many instances, the volume required will be so small as to render such a determination immaterial. A device designed to contain (and provide sustained release of) only the minimum required volume of drug-saturated carrier may be too small to manufacture and/or to handle. Thus, excess carrier, drug and/or an inert solid may have to be added in order to make the size of the device practical for manufacture and handling. When excess drug-saturated carrier is added, one must determine whether an extended delivery regimen is acceptable, and if it is not, the device must be removed at the end of the treatment period.

The overall design of the device can be determined by applying the release formula for a device of that shape according to Fick's First Law of Diffusion. The variable to be determined by solution of the equation will depend on whether device size or reservoir volume is the primary criterion.

For example, if a cylindrical implant is to be used, the volume of the reservoir will equal $\pi r_i^2 h$, wherein $r_i$ is the radius of the reservoir and h is its height. The formula for steady state release from a cylinder is:

$$[dQ/dt] = [2\pi h D K_d C_d]/[\ln(r_o/r_i)]$$

wherein:
$r_o$ is the outside radius of the cylinder, and
$C_d$ is the concentration of drug in the donor solution (i.e., the carrier). Steady state release is obtained when $C_d$ is maintained at saturation.

The thickness of the membrane needed for the desired sustained release is, therefore, $r_o - r_i$.

For a circular or oval-shaped ocular implant, where two sheets of membrane material are sealed around a reservoir, membrane thickness can be determined according to Fick's First Law of Diffusion, by use of the equation:

$$l = (APC_d dt)/dQ$$

wherein:
A is the surface area of the membrane, i.e., two times the surface area of one of its sides (this discounts the effect of permeation through the edge of the insert);
l is the membrane thickness (cm); and
$C_d$ is the concentration of the drug.

The Delayed/Sustained Release Formulations

The formulations of this invention include:
(A) a macromolecular active agent,
(B) a carrier in which the macromolecular active agent is mixed,
(C) a [co]polymer rate-limiting membrane, and
(D) a hydrating liquid, present in an amount predetermined to render the membrane structurally manipulable and/or substantially non-permeable to the active agent, all as described in greater detail below.

(A) The Active Agents

Macromolecular compositions suitable for delayed/sustained release using the devices of the present invention can generally be described as hydrophilic macromolecules having a molecular weight in excess of 1,000, particularly in the range of between 1,000 and 25,000. However, the principles of the invention are applicable to macromolecules having higher (and slightly lower) molecular weights. For example, suitable macromolecules include hormonally active polypeptides, e.g., luteinizing hormone-releasing hormone (LH-RH) polypeptides and analogs thereof, mammalian growth hormones, mammalian growth hormone-releasing hormones, and polypeptides having thymosin-like activity.

Hormonally active polypeptides are those peptides that have a specific regulatory effect on the activity of a certain body organ. Generally, they are secreted by an endocrine gland. Some peptides not secreted by an endocrine gland, however, exhibit a specific regulatory effect on a body organ and therefore are also classified as hormonally active compounds. Synthetically prepared analogues of naturally occurring, hormonally active polypeptides are to be considered as falling within the scope of this definition. Pharmaceutically acceptable salts of the naturally occurring hormones and their synthetic analogs that retain the same type of activity as their parent also are to be considered as within the scope of this invention.

Hormonally active peptides comprise a diverse group of proteins, but because of their functional specificity, they can conveniently be grouped into discrete classifications by physiological effect. Each protein group generally regulates one specific physiological function by interacting only with the organ or organs directly affecting that function. For example, LH-RH-active polypeptides act on the anterior pituitary gland to effect release of hormones that affect the activity of reproductive organs. Growth hormones act on the liver, causing it to release somatomedin, the peptide factor responsible for skeletal growth. Thymosin and thymically active peptides interact with the autoimmune system, enhancing the ability of the body's immune system to combat disease.

With regard to the specific hormonally active polypeptides of interest for delayed/sustained release with the present invention, in a first instance there is the naturally occurring luteinizing hormone-releasing hormone polypeptide and the synthetic analogs thereof.

The naturally occurring LH-RH peptide is produced in the hypothalmic region of the brain and controls the reproductive cycle of mammals by acting on the anterior pituitary gland to affect release of luteinizing hormone ("LH") and follicular stimulating hormone ("FSH"), which in turn act on the gonads to stimulate the synthesis of steroid hormones and to stimulate gamete maturation. The pulsatile release of LH-RH thereby controls the reproductive cycle in mammals. Additionally, LH-RH has effects in the placenta, in releasing human chorionic gonadotropin ("HCG"), and directly on the gonads.

Agonist analogs of LH-RH are useful for the control of fertility by two mechanisms of action. Low doses of LH-RH analogs can stimulate ovulation and are useful in the treatment of hypothalmic and ovulatory infertility. Additionally, they can be used for hypogonadal conditions and impotence, and for stimulating spermatogenesis and androgen production in the male.

Paradoxically, larger doses of highly potent and long-lasting analogs of LH-RH have an opposite effect, blocking ovulation in the female and suppressing spermatogenesis in the male. Related to these effects is a suppression of normal circulating levels of sexual steroids of gonadal origin, including reduction in accessory organ weight in the male and female. In domestic animals this paradoxical effect promotes weight gain in a feed-lot situation, stimulates abortion in pregnant animals and, in general, acts as a chemical sterilant. A full list of the paradoxical high dose effects of LH-RH and its analogs is set out in U.S. Pat. No. 4,234,571.

There is also a group of LH-RH analogs termed antagonists. These polypeptides have the paradoxical effect shown by LH-RH agonists, but at low dose levels relative to naturally occurring LH-RH. Such compounds are included within the scope of this invention.

The natural LH-RH peptide is a hydrophilic decapeptide comprised of naturally occurring amino acids (which have the L-configuration except for the achiral amino acid glycine). Its sequence is as follows: (pyro)-Glu-His-Trp-Ser-Tyr-Gly-Leu-Arg-Pro-Gly-NH$_2$.

Many analogs of this natural material have been studied. The beneficial effectiveness of these analogs has varied. The most significant modification where agonists are concerned is obtained by changing the 6-position residue from Gly to a D-amino acid, for example, D-Ala, D-Leu, D-Phe or D-Trp. Antagonist activity can be best realized by substituting the naturally occurring 2-position His amino acid residue with a D-amino acid residue. These analogs show increased activity relative to LH-RH.

In addition to modifications at position 6, increased agonist activity may be obtained by the following modifications: modifying position 10 to afford a nonapeptide as an alkyl-, cycloalkyl- or fluoroalkyl-amine, or by replacing Gly-NH$_2$ by an α-azaglycine amide; replacing tryptophan in position 3 by 3-(1-naphthyl)-L-alanine; and the substitution at position 6 of unnatural D-amino acid residues containing two or more carbocyclic aryl (or perhydroaryl) rings or a phenyl (or cyclohexyl) ring which is highly alkyl substituted. Substituting N-methyl-leucine for leucine in position 7 leads to increased stability towards enzymatic degradation, and substituting the position 5 tyrosine residue with phenylalanine or 3-(1-pentafluorophenyl)-L-alanine can be effected with retention of substantial biological activity. These specific compounds represent some of the more useful fertility-affecting LH-RH type polypeptides that have been developed to date. This is not intended to be an exhaustive or exclusive list of all LH-RH active polypeptides that have been made or that can or may be made. They are simply set out to illustrate the type of compounds which are the subject of this invention. Any or all of them can be interchangeably substituted into the compositions of this invention.

The LH-RH compounds of most interest herein are those from the last-mentioned group wherein the 6-position of the naturally occurring LH-RH material is replaced with a specific non-natural D-amino acid residue containing lipophilic carbocyclic residues, particularly residues containing two or more highly alkyl-substituted carbocyclic aryl (or perhydroaryl) rings, naphthyl or a phenyl (or cyclohexyl) ring. These particular polypeptides are the subject of U.S. Pat. No. 4,234,571 and are prepared in accordance with the procedures set forth therein. That patent is incorporated in full herein by reference and made a part of this application. Reference is made to that patent for a full description of the synthetic nonapeptides and decapeptides of most interest herein. A full description of the formulas, nomenclature and synthetic methods for preparing these compounds are found therein. The compounds there set out comprise the preferred embodiments of synthetic LH-RH analogs for incorporation into delayed/sustained- release formulations in this invention.

More specifically the LH-RH polypeptides of most interest in this invention are the nonapeptides and decapeptides of the formula:

(pyro)Glu-His-V-Ser-W-X-Y-Arg-Pro-Z and the pharmaceutically acceptable salts thereof wherein:

V is tryptophyl, phenylalanyl or 3-(1-naphthyl)-L-alanyl;

W is tyrosyl, phenylalanyl or 3-(1-pentafluorophenyl)-L-alanyl;

X is a D-amino acid residue of the formula:

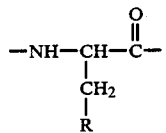

wherein R is:
(a) a carbocyclic aryl-containing radical selected from the group consisting of naphthyl, anthryl, fluorenyl, phenanthryl, biphenyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl; Y is leucyl, isoluecyl, nor-leucyl or N-methl-leucyl; Z is glycinamide or —NH—R$_1$, wherein R$_1$ is: lower alkyl, cycloalkyl, fluoro lower alkyl or has the formula:

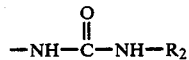

wherein R$_2$ is hydrogen or lower alkyl.

The preferred LH-RH-active synthetic nona and decapeptides of this invention are those wherein X is 3-(2-naphthyl)-D-alanyl or 3-(2,4,6-trimethylphenyl)-D-alanyl; Z is glycinamine, NHEt or aza-glycinamine; V is tryptophyl or phenylalanyl; W is tyrosyl; and Y is leucyl or N-methyl-leucyl.

Also of interest are the nonapeptides and decapeptides in which the following substitutions have been made: N-Ac-D-Nal(2) [N-Acetyl-3-(2-naphthyl)-D-alanyl] at position 1; D-p-Halo-Phe at position 2; D-Trp at position 3; D-Deh [D-Di-ethyl-homoarginyl] (optionally substituted at the alkyl position with a halogen) at position 6; and D-Ala or aza-Gly at position 10; these are described in U.S. Pat. Nos. 4,481,190 and 4,581,169, which are incorporated in full herein by reference and made a part of this application.

The most preferred compounds for LH-RH synthetic analogs are:

(pyro)Glu-His-Trp-Ser-Tyr-3-(2-naphthyl)-D-alanyl-Leu-Arg-Pro-Gly-NH$_2$,
(pyro)Glu-His-Trp-Ser-Tyr-3-(2-naphthyl)-D-alanyl-n-methyl-Leu-Arg-Pro-Gly-NH$_2$,
(pyro)Glu-His-Phe-Ser-Tyr-3-(2-naphthyl)-D-alanyl-Leu-Arg-Pro-Gly-NH$_2$,
(pyro)Glu-His-Trp-Ser-Tyr-3-(2,4,6-trimethylphenyl)-D-alanyl-Leu-Arg-Pro-Gly-NH$_2$,
(pyro)Glu-His-Trp-Ser-Tyr-3-(2-naphthyl)-D-alanyl-Leu-Arg-Pro-NHEt,
(pyro)Glu-His-Trp-Ser-Tyr-3-(2-naphthyl)-D-alanyl-N-methyl-Leu-Arg-Pro-NHEt,
(pyro)Glu-His-Trp-Ser-Tyr-3-(2-naphthyl)-D-alanyl-Leu-Arg-Pro-aza-Gly-NH$_2$,
(pyro)Glu-His-Trp-Ser-Tyr-D-Ala-Leu-Arg-Pro-Gly-NH$_2$,
(pyro)Glu-His-Trp-Ser-Tyr-D-Leu-Leu-Arg-Pro-Gly-NH$_2$,
(pyro)Glu-His-Trp-Ser-Tyr-D-Phe-Leu-Arg-Pro-Gly-NH$_2$,
(pyro)Glu-His-Trp-Ser-Tyr-D-Trp-Leu-Arg-Pro-Gly-NH$_2$,
N-Ac-D-Nal-(2)-D-p-Cl-Phe-Trp-Ser-Tyr-D-Deh-Leu-Arg-Pro-D-Ala-NH$_2$,
N-Ac-D-Nal-(2)-D-p-Cl-Phe-Trp-Ser-Tyr-D-F-Deh-Leu-Arg-Pro-D-Ala-NH$_2$,
N-Ac-D-Nal-(2)-D-p-F-Phe-Trp-Ser-Tyr-D-Deh-Leu-Arg-Pro-D-Ala-NH$_2$,
N-Ac-D-Nal(2)-D-p-Cl-Phe-Trp-Ser-Tyr-D-Deh-Leu-Arg-Pro-aza-Gly-NH$_2$,
and their pharmaceutically acceptable salts.

Especially preferred are (pyro)Glu-His-Trp-Ser-Tyr-3-(2-naphthyl)-D-alanyl-Leu-Arg-Pro-Gly-NH$_2$ and (pyro)Glu-His-Trp-Ser-Tyr-3-(2-naphthyl)-D-alanyl-Leu-Arg-Pro-aza-Gly-NH$_2$ and their pharmaceutically acceptable salts.

A second group of hormonally active polypeptides of interest herein are mammalian growth hormones. Growth hormones may be considered generally to be any substance which stimulates growth of the mammal when appropriately administered. The compounds of interest herein are those polypeptides secreted by the anterior pituitary gland, which exert an influence on protein, carbohydrate and lipid metabolism and control the rate of skeletal and visceral growth. Generally, growth hormones are species specific polypeptides with molecular weights falling between 22,000 and 24,000 daltons. In several species, for example, humans and cattle, the growth hormone also possesses some of the activities of lactogenic hormones.

Human Growth Hormone ("hGH") has been isolated, crystallized and characterized as a homogenous protein containing 191 amino acid residues and having a molecular weight of 22,128 daltons. It may be isolated from humans alone or with a much larger molecule which is probably an association of the primary polypeptide with another as yet unspecified protein. There are at least 4 isohormones of the primary molecule.

The reported amino acid content and sequence of hGH has undergone some revisions since the initial sequencing was carried out. At present hGH is described as being comprised of the following number and sequence of amino acids.

| | 5 | 10 | 15 | 20 | 25 | 30 |
|---|---|---|---|---|---|---|
| 1 | F P T I P | L S R L F | D N A M L | R A H R L | H Q L A F | D T Y Q E |
| 31 | F E E A Y | I P K E Q | K Y S F L | Q N P Q T | S L C F S | E S I P T |
| 61 | P S N R E | E T Q Q K | S N L Q L | L R I S L | L L I Q S | W L E P V |
| 91 | Q F L R S | V F A N S | L V Y G A | S N S D V | Y D L L K | D L E E G |
| 121 | I Q T L M | G R L E D | G S P R T | G Q I F K | Q T Y S K | F D T N S |
| 151 | H N D D A | L L K N Y | G L L Y C | F R K D M | D K V E T | F L R I V |
| 181 | Q C R S V | E G S C G | F | | | |

| COMPOSITION | | | |
|---|---|---|---|
| 7 ALA A | 14 GLN Q | 26 LEU L | 18 SER S |
| 11 ARG R | 13 GLU E | 9 LYS K | 10 THR T |
| 9 ASN M | 8 GLY G | 3 MET M | 1 TRP W |
| 11 ASP D | 3 HIS H | 13 PHE F | 8 TYR Y |
| 4 CYS C | 8 ILE I | 8 PRO P | 7 VAL V |
| MOL. WT. = 22,128 | | NUMBER OF RESIDUES = 191 | |

Two disulfide bridges are present in this molecule, one linking residues 67 and 165 and a second linking residues 182 and 189. The amino acid sequence given above is also set out in the *Atlas of Protein Sequence and Structure*, [Dayhoff, ed., 5 (Suppl. 3): 5–50 (National Biomedical Research Foundation, Washington, D.C., 1973)].

A subsequent publication by Martial, et al. [*Science*, 205: 602–607 (1979)], sets out the complementary DNA nucleotide sequence for hGH. This DNA sequence predicts glutamine, asparagine, glutamine, glutamic acid, glutamine, aspartic acid, asparagine, and glutamine at positions 29, 47, 49, 74, 91, 107, 109 and 122 respectively, while degradative protein sequencing indicates glutamic acid, aspartic acid, glutamic acid, glutamine, glutamic acid, asparagine, aspartic acid, and glutamic acid at these positions.

Availability of hGH has until recently been limited to that which could be extracted from the pituitary gland of human cadavers. However, recombinant DNA techniques have recently made it possible to produce biologically active hGH from bacteria in relatively substantial quantities. (See, for example, Martial, et al., supra.)

Bovine Growth Hormone ("bGH") has the same number of residues as hGH, 191, but there exist some differences in the amino acid residue sequence and in the numbers of particular residues. As set out in the Atlas of Protein Sequence and Structure, supra., bGH is comprised of the following sequence of amino acid residues:

are known in the art (for example, see Miller, et al., supra.)

In addition, this invention encompasses the growth hormones of sheep and horses. The amino acid residue sequence of both these hormones have been reported in the *Atlas of Protein Sequence and Structure*, supra., as follows:

| SHEEP GROWTH HORMONE | | | | | |
|---|---|---|---|---|---|
| 5 | 10 | 15 | 20 | 25 | 30 |
| 1 A F P A M | S L S G L | F A N A V | L R A Q H | L H Q L A | A D T F K |
| 31 E F E R T | Y I P E G | Q R Y S I | Q N T Q V | A F C F S | E T I P A |
| 61 P T G K N | E A Q Q K | S D L E L | L R I S L | L L I Q S | W L G P L |
| 91 Q F L S R | V F T D S | L V F G T | S D R V Y | E K L K D | L E E G I |
| 121 L A L M R | E L E D V | T P R A G | Q I L K Q | T Y D K F | D T N M R |
| 151 S D D A L | L K N Y G | L L S C F | R K D L H | K T E T Y | L R V M K |
| 181 C R R F G | E A S C A | F | | | |

| COMPOSITION | | | |
|---|---|---|---|
| 155 ALA A | 11 GLN Q | 27 LEU L | 13 SER S |
| 13 ARG R | 13 GLU E | 11 LYS K | 12 THR T |
| 5 ASN N | 9 Gly G | 4 MET M | 1 TRP W |
| 11 ASP D | 3 HIS H | 13 PHE F | 6 TYR Y |
| 4 CYS C | 7 ILE I | 6 PRO P | 7 VAL V |
| MOL. WT. = 21,859 | | NUMBER OF RESIDUES = 191 | |

| HORSE GROWTH HORMONE | | | | | |
|---|---|---|---|---|---|
| 5 | 10 | 15 | 20 | 25 | 30 |
| 1 F P A M P | L S S L F | A N A V L | R A Q H L | H Q L A A | D T Y K E |
| 31 F E R A Y | I P E G Q | R Y S I Q | N A Q A A | F C F S E | T I P A P |
| 61 T G K D E | A Q Q R S | D M E L L | R F S L L | L I Q S W | L G P V Q |
| 91 L L S R V | F T N S L | V F G T S | D R V Y E | K L R D L | E E G I Q |
| 121 A L M R E | L E D G S | P R A G Q | I L K Q T | Y D K F D | T N L R S |
| 151 D D A L L | K N Y G L | L S C F K | K D L H K | A E T Y L | R V M K C |
| 181 R R F V E | S S C A F | | | | |

| COMPOSITION | | | |
|---|---|---|---|
| 17 ALA A | 12 GLN Q | 26 LEU L | 15 SER S |
| 14 ARG R | 13 GLU E | 10 LYS K | 8 THR T |
| 5 ASN N | 8 GLY G | 4 MET M | 1 TRP W |
| 11 ASP D | 3 HIS H | 12 PHE F | 7 TYR Y |
| 4 CYS C | 6 ILE I | 7 PRO P | 7 VAL V |
| MOL. WT. = 21,757 | | NUMBER OF RESIDUES = 190 | |

These two growth hormones are presently available from the pituitary gland of the respective animals and are obtained by methods known in the art as set out, for

| BOVINE GROWTH HORMONE | | | | | |
|---|---|---|---|---|---|
| 5 | 10 | 15 | 20 | 25 | 30 |
| 1 A F P A | M S L S G | L F A N A | V L R A Q | H L H Q L | A A D T F K |
| 31 E F E R | T Y I P E | G Q R Y S | I Q N T Q | V A F C F | S E T I P A |
| 61 P T G K | N E A Q Q | K S D L E | L L R I S | L L L I Q | S W L G P L |
| 91 Q F L S | R V F T N | S L V F G | T S D R V | Y E K L K | D L E E G I |
| 121 L A L M | R E L E D | G T P R A | G Q I L K | Q T Y D K | F D T N M R |
| 151 S D D A | L L K N Y | G L L S C | F R K D L | H K T E T | Y L R V M K |
| 181 C R R F | G E A S C | A R | | | |

| COMPOSITION | | | |
|---|---|---|---|
| 15 ALA A | 11 GLN Q | 27 LEU L | 13 SER S |
| 13 ARG R | 13 GLU E | 11 LYS K | 12 THR T |
| 6 ASN N | 10 GLY G | 4 MET M | 1 TRP W |
| 10 ASP D | 3 HIS H | 13 PHE F | 6 TYR Y |
| 4 CYS C | 7 ILE I | 6 PRO P | 6 VAL V |
| MOL. WT. = 21,816 | NUMBER OF RESIDUES = 191 | | |

Molecular cloning of DNA complementary to bGH mRNA, as reported by Miller, et al. [*J. Biol. Chem.*, 255 (16): 7521–7524 (1980)], confirms this sequence except at positions 47 and 66 where aspartic acid and glutamic acid are replaced by their respective amides.

The primary source of bGH is the pituitary glands of slaughtered cattle. Methods of obtaining such materials example, in Miller, et al., supra.

Further of interest herein are short-chain peptides of 10–13 amino acids that demonstrate thymic activity. A number of substances are known which, when administered to animals, enhance the ability of an organism's immune system to combat disease. Among these substances are crude extracts of mycobacteria, glycopeptides and modifications of glycopeptides which are derived therefrom, and "thymosins," a family of hormones secreted by a thymosin gland. Recently, it has been shown that a fraction of blood, specifically, human serum prealbumin, also possesses such activity (U.S. Pat. No. 4,046,887).

The structure of human serum prealbumin is now clearly established. It is a tetramer of subunits, each which contains 127 amino acids in the same known sequence [Kanda, et al., *J. Biol. Chem.*, 249: 6796–6805 (1974)]; even the 3-dimensional configuration has been determined [Blake, et al., *J. Mol. Biol.*, 121 (3): 339 (1978)].

It has been found that the deca-, undeca-, dodeca-, and tridecapeptides that represent the N-terminal sequence in human serum prealbumin subunits are extremely potent in increasing immunological competence in mammals. Further, modification of the amino acid sequence of these peptides at one or more positions by substituting another amino-acyl residue for that normally present, results in a set of peptides with a similar or enhanced activity.

These peptides may be used clinically for human treatment in situations where immunologic competence is believed to be an important factor, for example, autoimmune diseases (e.g., lupus erythematosus, ulcerative colitis, autoimmune hemolytic anemia, thyrotoxicosis, rheumatoid arthritis, hepatic cirrhosis); thymic aplasia and dysplasia; augmentation of immunity of infectious (e.g., bacterial, viral and fungal) disorders; Hodgkin's disease, hypogammaglobulinemic syndrome; aberrant cell proliferative conditions; decrease in immunologic competence due to temporal decline in thymic hormone production; in chemical or radiologically induced immuno-suppressed states; and so forth.

Peptides having thymic activity and which are of interest in this invention can be represented by the formula:

wherein:
A, A' and A" are each independently Gly, D-Ala, D-Leu, or D-Trp, wherein A may optionally be N-alkylated or N-acylated;
B is Pro, Δ³-Pro, Thz, or diMeThz;
C and C' are each independently Thr, Ser, Val, or alloThr;
D is Glu, Gln, Asp, or Asn;
R is hydrogen, lower alkyl or lower acyl, substituted for one of the hydrogens on the ε-amino group of the lysyl residue;
X is Cys; Ala, ABU; or Cys(Me); and
Y is selected from the group consisting of hydroxy, Pro, Pro-Leu, and Pro-Leu-Met, —NH₂, ProNH₂, Pro-LeuNH₂ and Pro-leu-MetNH₂; and the pharmaceutically acceptable salts thereof.
Specifically, these peptides can be:

decapeptides of the formula:

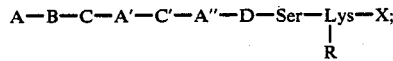

-continued undecapeptides of the formula,

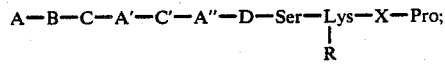

dodecapeptides of the formula,

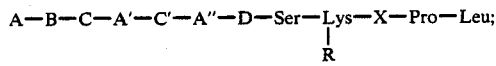

and tridecapeptides of the formula,

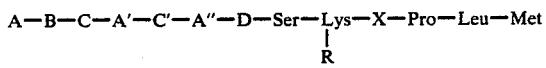

wherein A, A', A"; B; C; C'; D; R; and X are as defined above.

These synthetic peptides all demonstrate thymic activity. They are fully discussed and set out in U.S. Pat. No. 4,320,118. A full description of the nomenclature, synthetic methods, test procedures, a general and specific disclosure of the various synthetic peptides covered, a recitation of pharmaceutically acceptable salts for these peptides, and various other information necessary for a full and complete understanding of the scope of these peptides may be found there. That patent is incorporated in full herein by reference and made a part hereof.

A set of preferred embodiments of the thymosin-like decapeptides, undecapeptides, dodecapeptides, and tridecapeptides of this invention is that wherein A, A' and A" are each independently Gly, D-Leu, D-Trp or D-Ala, wherein A may optionally be alkylated or acylated at the α-amino group; B is Pro, C and C' are Thr; R is hydrogen, D is Glu, Gln, Asp or Asn; and X is Ala, Cys, or Cys(Me).

Especially preferred among these are those embodiments wherein A, A' and A" are each independently Gly or D-ala and wherein A may optionally be alkylated or acylated at the α-amino group; D is Glu or Gln and X is Ala or Cys. Another preferred set of embodiments is that wherein Y is —OH, —NH₂, Pro, or ProNH₂.

As set forth above and for convenience in describing these compounds, the conventional abbreviation for the various amino acids are used as generally accepted in the peptide art as recommended by the IUPAC-IUB Commission on Biochemical Nomenclature [*Biochemistry*, 11: 1726 (1972)] and represent the L-amino acids. All peptide sequences mentioned herein are written according to the generally accepted convention whereby the N-terminal amino acid is on the left and the C-terminal amino acid is on the right.

The macromolecular compositions of this invention will be present in the delayed/sustained release compositions in varying amounts, depending upon the effect desired.

Treatment of infertility with synthetic LH-RH peptides requires a low level of drug, while reduction of fertility and related effects requires a large dose relative to the activity of naturally occurring LH-RH. For LH-RH agonist fertility control it is desired to release the drug at such a rate that the subject will receive between about 0.01 and 100 μg/kg body weight per day, preferably between 0.1 and 5.0 μg/kg body weight per day.

Human growth hormone quantities necessary to effect normal growth have not been precisely defined at this point. HGH administered in amounts of about 0.1 to 10.0 Units (as defined by convention—based on biological activity for the particular hormone preparation—e.g., in one instance there are about 1.4 Units per mg of protein) per day based on body weight will effect increased linear growth in hGH-deficient children. A recent study by D. Rudman, et al. [*J. Clin. Endocrine Metabolism*, 49: 92–99 (1979)] has demonstrated the onset of increased linear growth in children known to be deficient in hGH and showing shorter stature and lower than average growth rates for their age groups by the administration of 0.3 to 3.0 Units of hGH per day.

Bovine, sheep or horse growth hormone may be administered on a daily basis in an amount anywhere between 5–100 mg/day. The dose may vary depending upon the activity of the growth hormone, the species, and the size of the animal.

Thymic peptides will be administered in the range of from about 10 ng/kg/day to about 20 mg/kg/day, preferably from about 100 ng/kg/day to about 5 mg/kg/day. Expressed in alternative terms for an average (70 kg) adult human subject, this would be from 700 ng/day to 1.4 g/day, preferably from 7 mg/day to 350 mg/day.

The compositions of this invention are formulated to contain the macromolecular active agents in an amount which may vary between 0.01 and 40.0 weight %. Preferably the agent will be present in the amount between 0.1 to 20.0 weight %.

The amount of macromolecular active agent placed in a particular formulation depends not only on the desired daily dose but also on the number of days that dose level is to be maintained. While this amount can be calculated empirically, the actual dose delivered is also a function of any interaction with the carrier and the membrane materials. Therefore the % weight of drug as stated herein represents an amount, which when taken in conjunction with a particular carrier and membrane, provides a desired release profile.

(B) The Carrier

Carriers useful in the practice of this invention are characterized in that the macromolecular composition should be at least partially soluble in them. A general range of about 0.1–1.0 g agent to about 0.5–3.0 ml carrier may be used. In the case of drug delivery devices, the carriers must be pharmaceutically or veterinarilly acceptable substances. These include solvents, aqueous systems, and solid substrates or matrices. In general, the carrier should be more permeable to the macromolecular composition than the rate-limiting membrane is.

Solvents useful as the carrier include, for example, oils such as silicone oil (particularly medical grade), corn oil, castor oil, peanut oil and sesame oil; condensation products of castor oil and ethylene oxide combining about 30 to 35 moles of ethylene oxide per mole of castor oil; liquid glyceryl triesters of a lower molecular weight fatty acid; lower alkanols; glycols; polyalkylene glycols.

The aqueous systems include, for example, sterile water, saline, dextrose, dextrose in water or saline, tear fluid and phosphate buffer, optionally in the presence of a suspending agent, for example, sodium carboxymethylcellulose, sodium alginate, poly(vinyl)pyrrolidone, and the like, alone or with suitable dispensing agents such as lecthin, polyoxyethylene stearate and the like. The presence of electrolytes in these aqueous systems may tend to lower the solubility of the macromolecular compounds in them.

The solid substrates or matrices include, for example, starch, gelatin, sugars (e.g., glucose), natural gums (e.g., acacia, sodium alginate, carboxymethyl cellulose), unpolymerized [co]monomers, [co]polymers (e.g., silicone rubber or enhanced permeability variations of the hydrogel membrane [co]polymers described below, so long as the carrier does not swell in the delivery environment to such an extent as to cause the membrane to rupture).

The carrier may also contain adjuvants such as preserving, stabilizing, wetting and emulsifying agents, and the like.

(C) The Rate-Limiting Membrane

The number and type of hydrogel rate-limiting [co]polymers which may be effectively used to practice this invention is limited only by the requirements that the material be biocompatible and non-biodegradable. That is, the polymer must be non-toxic to the host and must be of such composition that it is not degradable by the body.

[Co]monomers useful in the preparation of the rate-limiting membrane include:

| hydrophilic monomers | (50–100 mole %), |
| hydrophobic monomers | (0–50 mole %), and |
| crosslinker | (0–10 mole %). |

A presently preferred range for preparation of the rate-limiting membrane is:

| hydrophilic monomers | (75–100 mole %), |
| hydrophobic monomers (0–25 mole %), and | |
| crosslinker | (0–5 mole %). |

Presently the most preferred formulation for the rate-limiting membrane is:

| hydrophilic monomers | (100 mole %), and |
| crosslinker | (0.32 mole %). |

The mole % of crosslinker is sometimes calculated based on the total number of moles of [co]monomer being 100%; i.e., the mixture can contain more than 100 mole % after the crosslinker (and/or, e.g., a polymerization initiator) has been added.

Essentially, the selection and ratios of these ingredients can be varied to tailor the membrane to the macromolecular composition to be dispensed, taking into account its molecular weight, polar characteristics, and hydrophilicity. Thus, the approximate sizes of the interstitial spaces in the xerogel, the partially hydrated hydrogel, and the fully hydrated hydrogel may be predetermined (relative to the diffusability of the macromolecular composition). For example, a non-crosslinked hydrophilic homopolymer would be expected to have the largest pore sizes and greatest ability to swell, but ultimately, may tend to dissolve. The addition of crosslinking agent would render the hydrogel somewhat more rigid and limit the swellability of the hydrogel, thereby limiting the expansion of the interstitial spaces. The addition of a hydrophobic comonomer would enhance this restriction even further.

The hydrophilic monomers include, for example, acrylic and/or methacrylic acid and the water soluble derivatives thereof, such as hydroxyalkyl esters and amides where alkyl is 1 to 4 carbon atoms (e.g., N-hydroxymethyl(meth)acrylate, N-hydroxymethyl(meth)acrylamide, 2-hydroxyethyl(meth)acrylate, 2-hydroxyethyl(meth)acrylamide, 2-hydroxypropyl(meth)acrylate, 2-hydroxypropyl(meth)acrylamide, 3-hydroxypropyl(meth)acrylate, 3-hydroxypropyl(meth)acrylamide, and 2,3-dihydroxypropyl(meth)acrylamide, and the like), glycerol (meth)acrylate, glycidyl (meth)acrylate, monoolefinic derivatives of heterocyclic nitrogen-containing monomers (e.g., N-vinylpyrrole, N-vinylsuccinimide, 1-vinyl-2-pyrrolidone) and other commonly used biocompatible hydrophilic monomers.

The most preferred hydrophilic monomers are 2-hydroxyethylmethacrylate ("HEMA") and glycerol methacrylate ("GMA").

The hydrophobic monomers include, for example, acrylic- and methacrylic esters and amides of monohydric linear or branched alcohols with from 1 to 2 carbon atoms, and which alcohols may be aliphatic, cycloaliphatic, or aromatic in nature (for example, methyl-, ethyl-, propyl-, iso-propyl-, n-, iso- and tertiary butyl-, hexyl-, pentyl-, 2-ethylhexyl, cyclohexyl, stearyl-, phenyl-, benzyl-, methoxyethyl-, glycidyl-acrylate or methacrylate, as well as the corresponding amides) and the fumarate, maleate and itaconate di-esters thereof, vinyl esters (e.g., vinyl acetate, vinyl propionate, and vinyl benzoate), and vinyl ethers (e.g., methyl-, ethyl-, propyl-, butyl-, and methoxyethyl-vinyl ether).

The crosslinkers (or crosslinking monomers or agents) include, for example, insoluble di- or polyacrylates and methacrylates of diols and polyols [e.g., ethyleneglycoldimethacrylate ("EGDMA") and tetraethyleneglycoldimethacrylate ("TEGDMA")].

(D) The Hydrating Liquid

The hydrating liquid useful in the practice of the invention is typically a liquid simulating the environment in which the macromolecule will be released. For example, sterile water, tear fluid, saline solution, phosphate buffer solution, and the like may be used. While liquids other than water are useful as the hydrating liquid, the degree to which a membrane is hydrated is referred to as its "water content".

The compositions of this invention exhibit sustained release of the macromolecular compounds over extended periods of time. This time period may range, for example, from one week to 3 years depending on the desired administration regimen. Preferably the release time will be about 1 week to 24 months.

EXAMPLES

The following examples are given to enable those skilled in the art to more clearly understand and to practice the present invention. They should not be considered as a limitation on the scope of the invention, but merely as being illustrative and representative thereof.

The compositions and devices of the present invention have been evaluated by preparing a variety of hydrogel rate-limiting membranes (in the form of films) and testing the permeability of those films to macromolecular compositions suspended in different carrier systems, under different hydration conditions.

EXAMPLE I

HEMA/MMA Cast Copolymers

This example illustrates the preparation of rate-limiting membrane [co]polymer materials by the casting method.

HEMA/MMA [co]monomers were mixed in the molar ratios shown in Table I, by mixing molar percentages of the monomers (for a total of 10 g) in toluene (150 ml). Each reaction mixture was purged of oxygen by bubbling with nitrogen. Polymerization was initiated by the addition of 0.024 g (0.146 mmol) of azobisisobutironitryl and continued in a well-sealed pressurized vessel at 65° for 24 hours. The respective [co]polymers precipitated, were separated by filtration and allowed to dry at room temperature for 48 hours. The [co]polymers were purified by precipitation in water (500 ml) from 20% w/v solution of [co]polymer in $CH_2Cl_2$:methanol (1:4) solution (10 ml), and then dried under vacuum at 50° C. Copolymers prepared with greater than 50% starting MMA gave polymerization yields below 50%; they were not pursued further.

Film fabrication was carried out by dissolving the [co]polymers in 20% $CH_2Cl_2$ in methanol (1.0 g in 5.0 ml solvent) and pouring the dissolved solution onto clean glass plates coated with teflon foil. The films were covered (with another teflon-coated glass plate, held a desired distance apart from the first plate by a silicon rubber gasket) and allowed to dry for 24 hours under ambient conditions. The dry films separated easily from the plates. They were hydrated by immersion in distilled water at room temperature. The equilibrium water contents of the films were determined by comparing dry weight and fully-saturated weight, and are reported in Table I. Membrane thicknesses of about 0.08 mm were measured using a mechanical micrometer.

TABLE I

| Comonomer Feed Composition Molar % MMA | Cast Copolymer Equilibrium Water % |
|---|---|
| 0.0 | — |
| 25.0 | 42.1 ± 2.0 |
| 25.0 | 39.2 ± 0.9 |
| 40.0 | 34.5 ± 1.6 |
| 50.0 | 30.1 ± 2.0 |

EXAMPLE II

HEMA/MMA Redox Copolymers

This example illustrates the preparation of rate-limiting membrane [co]polymer materials by the in situ redox method, using the redox polymerization catalyst $Na_2S_2O_5/K_2S_2O_8$ and an accelerator $Fe(NH_4)_2(SO_4)_2\cdot 6H_2O$.

HEMA/MMA [co]monomers were mixed in the molar ratios shown in Table II, by mixing the appropriate molar weight percentages of the [co]monomers with 0.25 ml of aqueous $K_2S_2O_8$ and 0.12 ml of the accelerator in a glass vial. Nitrogen was bubbled through the mixture for 10 minutes, to purge it of oxygen. Then, the remaining catalyst, 0.25 ml of $Na_2S_2O_5$, was added and the mixture was shaken vigorously. The mixture was poured immediately between sealed, teflon-coated glass plates (separated by a selected distance) at room temperature. After a few minutes the mixture solidified.

The reaction was allowed to proceed for 24 hours. The flexible uniform films were removed easily from the coated plates. The equilibrium water contents of the films were determined by comparing dry weight and fully saturated weight, and are reported in Table II.

TABLE II

| Comonomer Feed Composition Molar % MMA | Redox Copolymer Equilibrium Water % |
|---|---|
| 0.0 | 39.1 ± 1.1 |
| 2.5* | 35.5 ± 1.3 |
| 5.0 | 38.7 ± 1.2 |
| 7.5* | 33.2 ± 0.9 |
| 10.0 | 34.0 ± 1.6 |
| 10.0* | 30.4 ± 1.1 |
| 15.0 | 32.4 ± 1.1 |
| 20.0 | 32.6 ± 1.2 |
| 30.0 | 24.6 ± 0.6 |

*Prepared as part of a separate batch

The films containing up to 20% MMA were strong, homogeneous and had uniform thickness; they were stable and flexible, and did not expand during the later diffusion experiments. The film of 30% MMA was not homogeneous and, therefore, not pursued further. All of the films were insoluble in methanol, but swelled very well in that solvent. This one-step method gave strong uniform films, and is presently preferred.

EXAMPLE III

Crosslinked HEMA Redox Homopolymers

This example illustrates the preparation of rate-limiting membrane crosslinked HEMA homopolymer materials by the in situ redox method of Example II.

EGDMA crosslinker and HEMA monomer were mixed in the molar ratios shown in Table III.

TABLE III

| Crosslinker Feed Composition Molar % EGDMA | Redox Polymer Equilibrium Water % |
|---|---|
| 0.0 | 39.1 |
| 0.0* | 40.2 ± 1.0 |
| 0.5* | 35.5 ± 1.0 |
| 1.0 | 33.7 |
| 2.0* | 32.1 ± 1.6 |
| 3.0 | 30.8 |
| 4.0 | 24.9 |
| 5.0 | 22.8 |

*Prepared as part of a separate batch

The resulting films were very strong, uniform and stable. Crosslinked films were preferred and more practical to use for diffusion experiments. The crosslinked HEMA homopolymers are also presently preferred as the rate-limiting membrane material.

EXAMPLE IV

Diffusion Studies

Films were prepared as described in Examples I, II and III. They were tested for the diffusion of a macromolecular composition (nafarelin acetate).

The experiments were performed in a two-compartment vertical glass cell. The upper compartment had a volume of 3 ml and was used to contain the donor solution. The bottom compartment had a volume of 8.5 ml and was used to contain the receptor solution; it was also equipped with a stirring rod and a side arm for withdrawing aliquots. Each membrane was put between two soft silicone rubber gaskets (to avoid damage) and was clamped in place between the two compartments of its cell.

For each experiment, the upper and lower chambers were filled with 2.0 and 8.5 ml of isotonic pH 7.40 phosphate buffer solution (prepared by dissolving 3.40 g $KH_2PO_4$ and 14.44 g $Na_2HPO_4$ in distilled water, bringing the volume to 1,000 ml). Each cell was immersed in a water bath at 37° C., with constant stirring, and allowed to equilibrate for 48 hours. The upper compartment's solution was then replaced with a donor solution of nafarelin acetate (210 μg/ml) in the pH 7.40 buffer solution.

At sampling, 1 ml aliquots were removed from the flask through the side arm and diluted to 2.0 ml with $CH_3CN$:0.173M $KH_2PO_4$ (46:64). The aliquot was analyzed for nafarelin acetate by HPLC at 225 nm. The aliquot volume was replaced by the addition of fresh buffer solution to the lower chamber.

The flux of nafarelin acetate through the membranes, their permeability coefficients and the release delay times were calculated from the data obtained in the diffusion studies.

Figure 2:
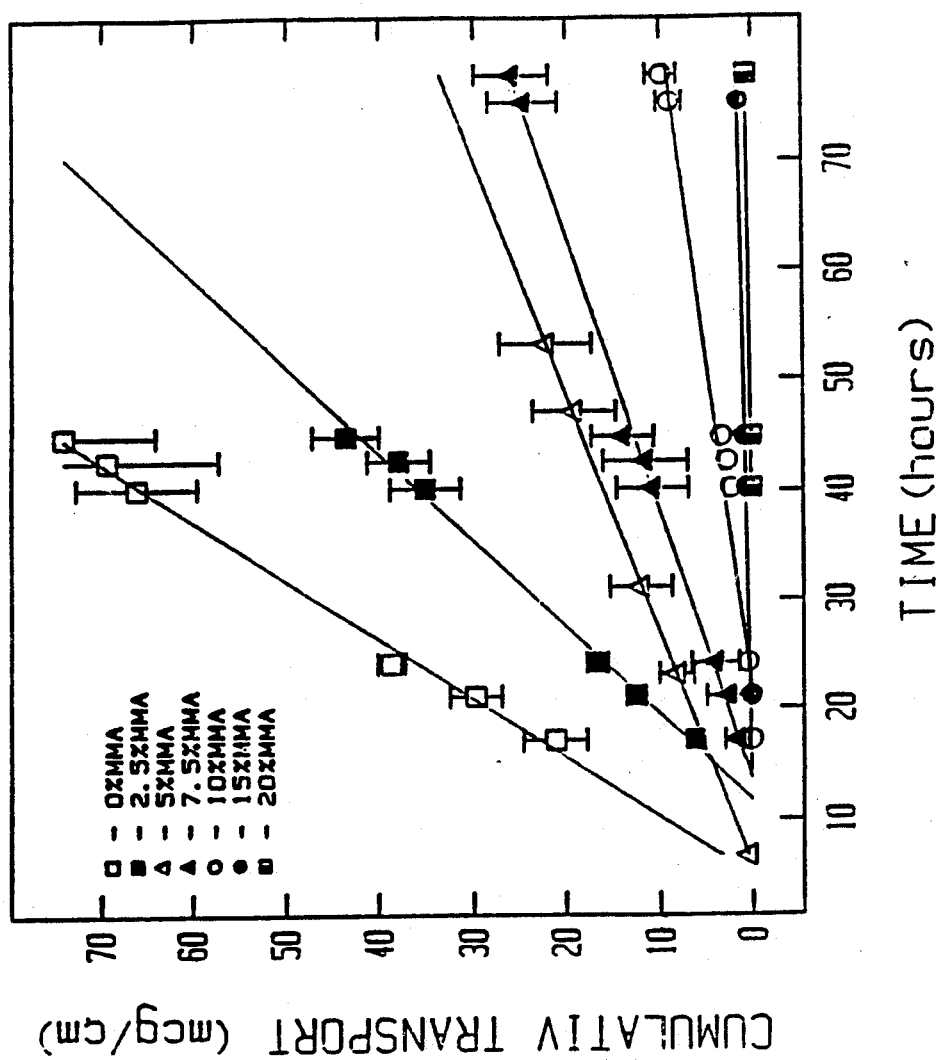
FIG. 2 is a graph showing cumulative transport vs. time, for the macromolecular composition nafarelin acetate through HEMA/MMA redox copolymer rate-limiting membranes, prepared in accordance with the present invention.
Figure 3:
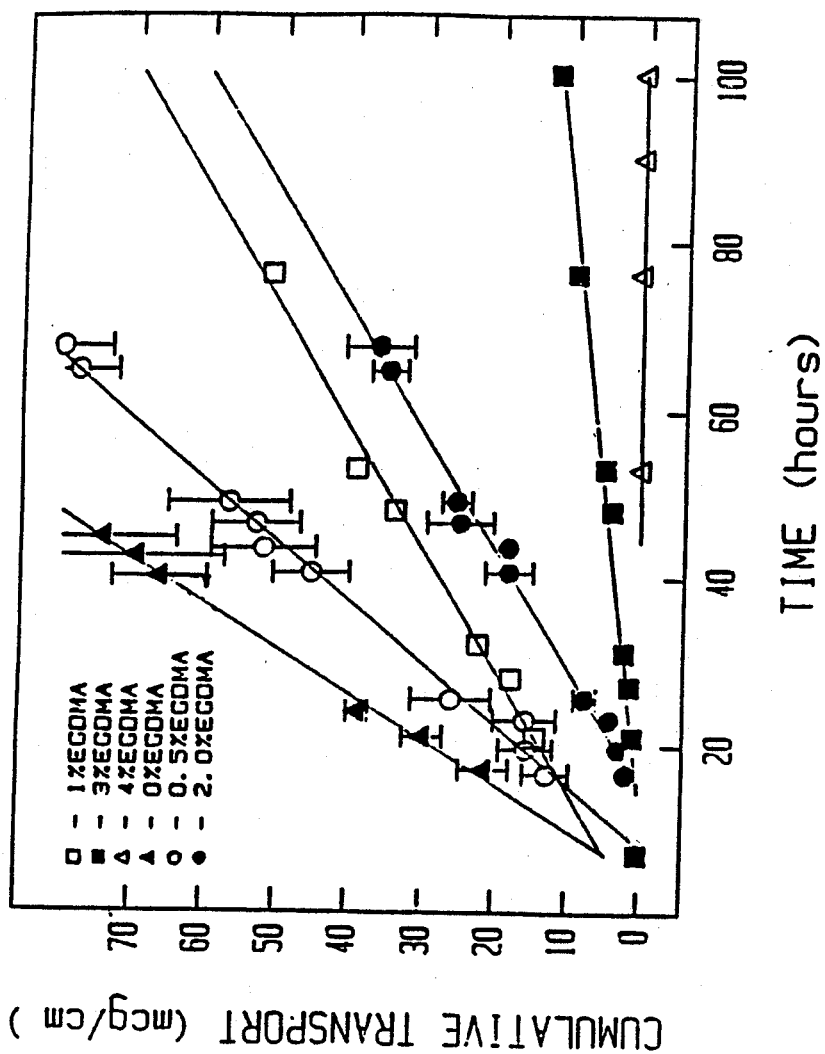
FIG. 3 is a graph showing cumulative transport vs. time, for the macromolecular composition nafarelin acetate through crosslinked HEMA redox homopolymer rate-limiting membranes, prepared in accordance with the present invention.
Figure 4:
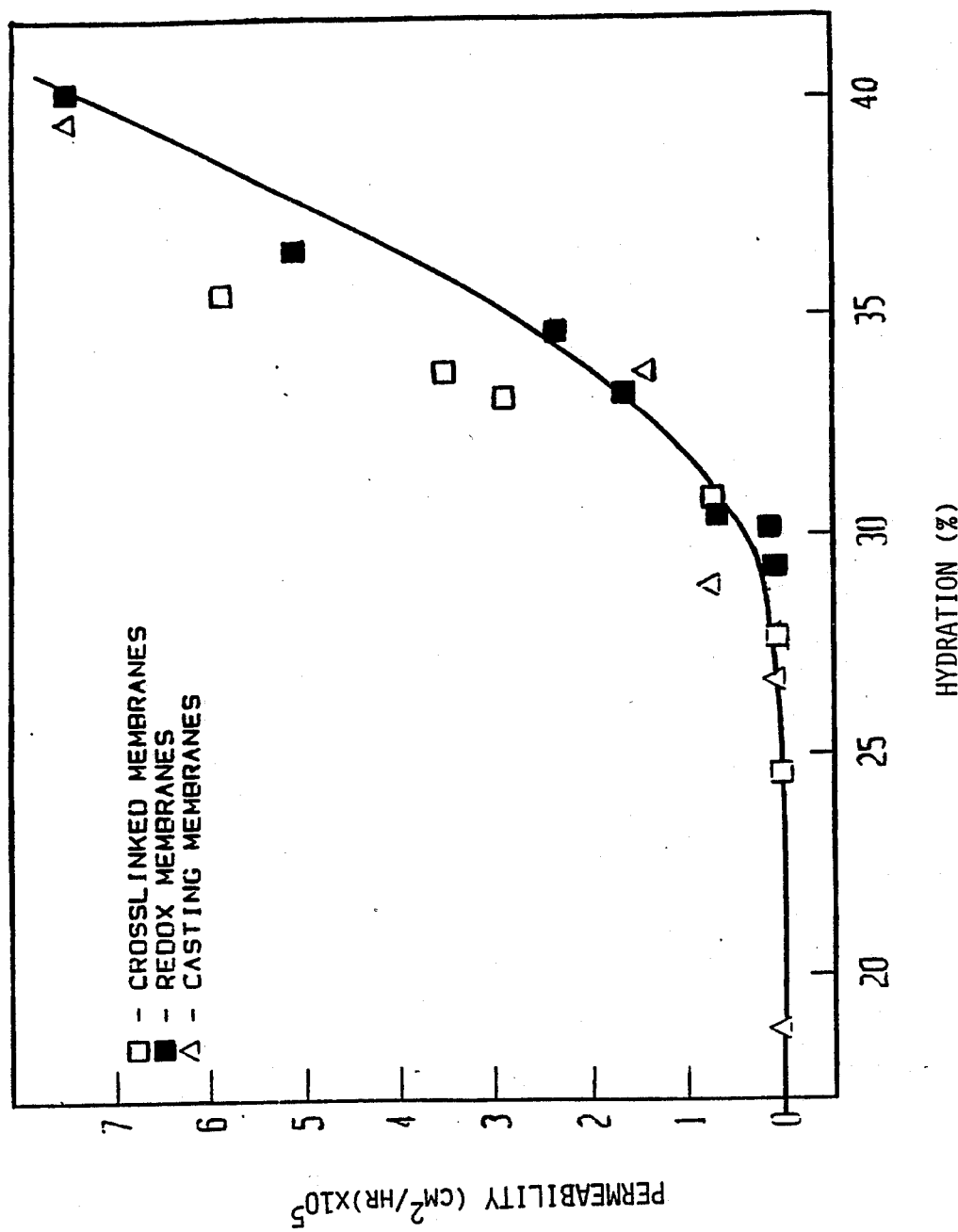
FIG. 4 is a plot of the permeability of nafarelin acetate vs. equilibrium water content of rate-limiting membranes, prepared in accordance with the present invention.

The cumulative transport vs. time was plotted for each of the membranes tested. Cumulative transport through the HEMA/MMA cast copolymers is shown in FIG. 1. Cumulative transport through the HEMA/MMA redox copolymers is shown in FIG. 2. Cumulative transport through the crosslinked HEMA homopolymers is shown in FIG. 3. FIG. 4 is a plot of the permeability of nafarelin acetate vs. equilibrium water content, from which the % $H_d$ was determined (about 29% for this system).

As shown in FIG. 4, the water content is determinative of permeability; for nafarelin acetate, very low permeability was detected at water content levels below about 30%, with dramatic increases above that. As pointed out above, the specific percentages at which release will begin depend largely on the characteristics of the macromolecular composition, and also on the [co]polymer composition.

Table IV summarizes these results. Flux per unit area was determined from the slope of the linear portion of the curves (dQ/Adt) and the permeability coefficient "P" was calculated ([dQ/Adt](l)/$C_d$).

TABLE IV

| Membrane Content | Hydration % | Flux (μg/cm²/hr) | P (ml/hr) | Release Delay Time (hr) |
|---|---|---|---|---|
| Cast Copolymers | | | | |
| 10.2% MMA | 39.5 ± 1.2 | 1.4964 | 7.48 | 1 |
| 14.6% MMA | 33.7 ± 1.8 | 0.2778 | 1.39 | 2 |
| 20.6% MMA | 28.8 ± 1.1 | 0.1461 | 0.73 | 4 |
| 33.6% MMA | 26.6 ± 0.8 | 0.0107 | 0.05 | 45 |
| 36.4% MMA | 18.7 ± 0.5 | 0 | 0 | >100 |

TABLE IV-continued

| Membrane Content | Hydration % | Flux (μg/cm²/hr) | P (ml/hr) | Release Delay Time (hr) |
|---|---|---|---|---|
| Redox Copolymers | | | | |
| 2.5% MMA | 36.5 ± 1.3 | 1.2615 | 5.1 | 6 |
| 5.0% MMA | 34.6 ± 1.0 | 0.4660 | 2.33 | 11.6 |
| 7.5% MMA | 33.2 ± 0.9 | 0.4040 | 1.63 | 13.2 |
| 10.0% MMA | 30.4 ± 1.1 | 0.1639 | 0.66 | 23 |
| 15.0% MMA | 30.1 ± 0.8 | 0.0231 | 0.12 | 30 |
| 20.0% MMA | 29.2 ± 0.6 | 0.0140 | 0.07 | 42 |
| Crosslinked Redox Polymers | | | | |
| 0.0% EGDMA | 40.2 ± 1.0 | 1.8583 | 7.51 | 5.2 |
| 0.5% EGDMA | 35.5 ± 1.1 | 1.3806 | 5.58 | 5.3 |
| 1.0% EGDMA | 33.7 | 0.6996 | 3.50 | 3 |
| 2.0% EGDMA | 33.1 ± 0.8 | 0.7079 | 2.87 | 14.7 |
| 3.0% EGDMA | 30.8 ± 1.4 | 0.1411 | 0.71 | 27 |
| 4.0% EGDMA | 27.6 | 0.0082 | 0.04 | 55 |
| 5.0% EGDMA | 24.6 | 0.0 | 0.0 | >100 |

In Table IV, the % MMA content in the Cast Copolymers is expressed in units of mole percent MMA in the polymerized copolymer, as determined by NMR. This was determined because a significant loss of MMA during polymerization was suspected. The content of the Redox [Co]polymers is expressed as molar percents in the [co]monomer feed.

The data demonstrates the ability of membranes prepared in accordance with the present invention to give a delayed/sustained release of macromolecular compositions. As illustrated, the time delay until diffusion occurs increases proportionally with the increase in structural rigidity of the polymer material, i.e., as the hydrophobic monomer's concentration and/or the degree of crosslinking is increased, and inversely with the percent hydration of the material.

EXAMPLE V

Cylindrical Device Design for Nafarelin Acetate

Using the data reported in Table IV, 12 month reservoir-type devices for delivery of the pharmaceutical macromolecular composition nafarelin acetate are designed as follows, for rate-limiting membranes prepared in accordance with Example I–III.

To deliver 16 μg/day of nafarelin acetate at least 5860 μg must be placed in the reservoir. Preferred dimensions for the device are approximately 2.5 cm in height and 0.5 cm in diameter. This size device will hold the required 5860 μg of nafarelin acetate suspended in silicone oil. It has also been found that devices of these approximate dimensions polymerize well.

This data is applied to the equation for steady state delivery from a cylindrical device:

$$[dQ/dt] = [2\pi h D K_d C_d]/[\ln(r_o/r_i)]$$

using the following data:
- $dQ/dt = 0.666$ μg/hr;
- $C_d = 1.40$ mg/ml
- $P = DK_d$ (Results taken from Table IV)
- $r_o = 0.27$ cm
- $r_i =$ (Reported in Table V)

TABLE V

| Membrane Sample | P | $r_i$ (cm) | Membrane Thickness (cm) |
|---|---|---|---|
| Cast Copolymers | | | |
| 10.2% MMA | 7.48 | 0.0307 | 0.2392 |
| 14.5% MMA | 1.39 | 0.1803 | 0.0897 |
| 20.6% MMA | 0.73 | 0.2184 | 0.0516 |
| Redox Copolymers | | | |
| 2.5% MMA | 5.10 | 0.06145 | 0.2086 |
| 5.0% MMA | 2.33 | 0.1372 | 0.1328 |
| 7.5% MMA | 1.63 | 0.1682 | 0.1018 |
| Crosslinked Redox Copolymers | | | |
| 0.0% EGDMA | 7.51 | 0.0306 | 0.2394 |
| 0.5% EG0MA | 5.58 | 0.0534 | 0.2166 |
| 1.0% EGDMA | 3.50 | 0.0977 | 0.1723 |
| 2.0% GGDMA | 2.87 | 0.1173 | 0.1527 |

EXAMPLE VI

Cylindrical Device Design for Aza-Gly[10] Nafarelin Acetate

By substituting an equivalent quantity of the veterinary macromolecular composition aza-Gly[10]-nafarelin acetate for the nafarelin acetate in Example V, a 12 month veterinary delivery device can be designed, for rate limiting membranes prepared in accordance with Examples I–III.

EXAMPLE VII

Monolithic Ocular Insert Device

This example illustrates the preparation of monolithic devices for the delayed/sustained release of nafarelin acetate at a rate of at least 1 μg/hr over 7 days. The devices' sizes were particularly adapted for use as an ocular insert, for delivery of the macromolecular drug composition through the ocular/nasal route. The devices' compositions were as follows:

| nafarelin acetate | variable |
|---|---|
| HEMA | 0.328 ml |
| EGDMA | 0.017 ml |
| 1% aqueous $K_2S_2O_8$ | 0.052 ml |
| 0.075% aqueous $Fe(NH_4)_2(SO_4)_2$ | 0.017 ml |
| 2% aqueous $Na_2S_2O_5$ | 0.052 ml |

Aqueous solutions of $Fe(NH_4)_2(SO_4)_2$ and $K_2S_2O_8$ were prepared and mixed, followed by the addition of the HEMA and EGDMA. The mixture was purged with nitrogen for 10 minutes. The aqueous solution of $Na_2S_2O_5$ was then added. 0.4 ml of the resulting solution was rapidly added to a vial containing the nafarelin acetate. Upon dissolution of the compound, the solution was injected between teflon-coated glass plates separated with a 0.5 mm gasket, and was allowed to cure at room temperature for 24 hours under an atmosphere of nitrogen. A clear uniform film was obtained, and was cut into oval-shaped monolithic devices suitable for both in vitro and in vivo studies. The devices were sterilized with 1.25 Mrad of gamma irradiation. The devices' specifications were as follows:

|  | Device #1 | Device #2 |
| --- | --- | --- |
| Weight | 0.02 g | 0.02 g |
| Thickness | 0.44 mm | 0.44 mm |
| Length | 1.4 mm | 1.4 mm |
| Width | 0.4 cm | 0.4 cm |
| Area (single side) | 0.4 cm$^2$ | 0.4 cm$^2$ |
| Nafarelin acetate | 1.3 mg | 2.0 mg |

The devices were incubated in isotonic phosphate buffer at pH 7.4 at 37° C. Assays of the phosphate buffer receptor medium were taken to determine the presence of nafarelin acetate. The results of those assays are presented in Table VI.

TABLE VI

| Hours | Device #1 | Device #2 |
| --- | --- | --- |
| 2.3 | 26.7 | 51.3 |
| 5.0 | 17.0 | 26.8 |
| 22.0 | 7.0 | 13.6 |
| 27.0 | 6.1 | 9.6 |
| 43.0 | 4.1 | 7.2 |
| 51.0 | 3.5 | 5.9 |
| 115.0 | 2.2 | 3.5 |
| 140.0 | 1.6 | 3.1 |
| 189.0 | 1.0 | 1.7 |

The devices successfully delivered the macromolecular drug at a rate of 1 μg/hr for over seven days. These devices were designed for non-zero order release. Zero order release may be obtained by treating these devices as drug-saturated solid carriers and surrounding them with a rate-controlling membrane, as described above.

EXAMPLE VIII

Reservoir Device

A cylindrical reservoir-type device for the sustained delivery of a macromolecular composition, e.g., nafarelin acetate, over a one year period, is made as follows:

Crosslinked HEMA polymer is prepared according to Example III, by combining the following:

| 3.1 ml | HEMA |
| --- | --- |
| 0.6 ml | 1% K$_2$S$_2$O$_8$ (aq) |
| 15 μl | EGDMA |
| 10 μl | 0.0075% Fe(NH$_2$)$_2$(SO$_4$)$_2$ (aq) |

Nitrogen is bubbled through the mixture for 10 minutes, followed by the addition of 0.6 ml of 2% aqueous Na$_2$S$_2$O$_5$. The mixture is transferred to a cylindrical mold (either with or without a hollow core) and allowed to polymerize at room temperature for 24 hours, under nitrogen. The polymerized cylinders are removed from the mold. When a mold without a core is used, a core is then drilled into the cylinder. The core must be drilled (or the mold designed) so that the wall thickness of the cylinder will have the dimension desired for the release profile of the device.

A suspension of macromolecular composition is made in silicone oil, by adding, e.g., 30.0 mg nafarelin acetate into 0.3 ml of silicone oil (Dow Corning 360 Medical Fluid-visocity 1,000 cP), optionally sonicating, and shaking well to obtain a milky, homogeneous suspension. The reservoirs are filled with an amount of the suspended drug sufficient to carry out the treatment regimen.

A fresh HEMA/EGDMA mixture is prepared, as described above, and carefully added to the tops of the reservoirs (without disturbing the drug-suspended carrier). The topped-off cylinders are allowed to polymerize for 24 hours at room temperature, under nitrogen, to effect a seal.

The cylindrical devices give a predictable, delayed/-sustained release of the macromolecular composition.

EXAMPLE IX

Alternative Suspension Procedure

Cylindrical reservoir devices can be fabricated in accordance with Example VIII by substituting the following procedure for the drug suspension and reservoir filling steps described therein:

A predetermined amount (depending on the treatment regime) of the macromolecular composition (e.g., 20–40 mg of dry nafarelin acetate) is added to the reservoir. An appropriate amount (depending on the size of the reservoir) of a liquid carrier (e.g., 0.3 ml of Dow Corning 360 Medical Fluid) is then added to the drug-filled reservoir.

The reservoir sealing procedure of Example VIII is then followed.

EXAMPLE X

Alternative Reservoir Devices

Alternative reservoir deviced can be fabricated by following the procedure outlined in Example VII, and substituting the following alternative active agent/carrier combinations for nafarelin acetate:

| thymosin - 1 mo | 1.0 g/1.0 ml Si Oil |
| --- | --- |
| sheep growth hormone - ½ yr | 2.0 g/3.0 ml Si Oil |
| horse growth hormone - ½ yr | 10.0 g/10.0 ml Si Oil |
| bovine growth hormone - ½ yr | 15.0 g/15.0 ml Si Oil |
| human growth hormone - 1 yr | 500 Units/0.6 ml Si Oil |
| aza-Gly$^{10}$-nafarelin acetate - 1 yr | 30.0 mg/0.3 ml Si Oil |

EXAMPLE XI

Preparation of Reservoir Devices

Polymer rods were prepared by casting a polymerization mixture of:

| HEMA | 6.25 ml |
| --- | --- |
| EGDMA | 40.0 μl |
| H$_2$O | 0.80 ml |
| 2% aqueous K$_2$S$_2$O$_8$ | 0.50 ml |
| 0.075% aqueous Fe(NH$_4$)$_2$(SO$_4$)$_2$ | 15.0 μl |
| 4% aqueous Na$_2$S$_2$O$_5$ | 0.50 ml | into a series of small glass vials (about 1.2"×0.25"), which were allowed to cure at room temperature for 24 hours. The glass vials were then broken and smooth, clear polymer rods (2.5 cm long and 6.0 mm in diameter) were obtained. The rods were placed in a dessicator containing a concentrated (i.e., saturated) solution of CaCl$_2$ in water, at a humidity of 32%, for about 6 hours.

The rods were removed from the dessicator and carefully drilled to form a reservoir having a diameter of 4.0 mm, proceeding with the drill in about 0.5 cm steps, followed by removal of the drill bit from the rod for cooling (by immersion in water or by application of a cold air) before commencing the next 0.5 cm step. Drilling is continued until a reservoir of sufficient volume is formed, in no event drilling closer to the end of the rod than the thickness of the reservoir (i.e., 2.0 mm). It was observed that having the rods in a partially hydrated state was of significant benefit for the drilling operation. Fully hydrated rods were found to be too flexible and soft. Dry rods were found to be too stiff and easy to crack during drilling.

2.0 mg of dry aza-Gly$^{10}$-nafarelin acetate was added to each of the hollow cylinders (having water contents of about 12% to 15%). About 0.2 ml of silicone oil (having a viscosity of 350 cP) was injected into each cylinder, filling each to an internal height of about 2.0 cm and taking care not to wet the top of the cylinders.

The cylinders were then sealed by floating a few drops of a polymerization mixture, as described above, on top of the silicone oil. In order to inhibit swelling from taking place, the tops of the cylinders were covered with parafin paper to stabilize their dimensions. Also, 80 $\mu$l of the $Fe(NH_4)_2(SO_4)_2$ accelerator was used in the polymerization mixture to expedite the polymerization process. The sealed cylinders were allowed to polymerize at room temperature for 24 hours.

The devices so formed were each put into 2.5 ml of a pH 7.40 isotonic phosphate buffer solution in a cell and kept in a shaking water bath at 37° C. The release of aza-Gly$^{10}$-nafarelin acetate was measured over time (at 15, 22 and 34 days) by removing the buffer from the cells (replacing it with an equal amount of fresh buffer) and measuring for the presence of solute by HPLC. No solute was detected in the buffer at 15 days. At 22 days, the devices fabricated with 350 cP silicone oil showed release of about 0.36 $\mu$g of solute and at 34 days these devices showed release of about 1.0 $\mu$g of solute. It was concluded that while delayed/sustained release had been demonstrated, use of a thinner rate-controlling membrane and a greater starting amount of active agent would be preferable.

While the present invention has been described with reference to specific embodiments thereof, it should be understood by those skilled in the art that various changes may be made and equivalents substituted without departing from the true spirit and scope of the invention. All such modifications are intended to be within the scope of the claims appended hereto.

What is claimed is:

1. A drug delivery device for the controlled administration of a macromolecular drug, said device comprising:
    (a) a pharmaceutically acceptable carrier;
    (b) a macromolecular drug having a molecular weight greater than about 1,000 mixed with said carrier; and
    (c) an initially partially-hydrated, non-biodegradable, hydrogel rate-limiting membrane, wherein said membrane:
        (i) comprises a homopolymer or a copolymer material surrounding said carrier and drug, and
        (ii) has an initial water content such that it is substantially non-permeable to said macromolecular drug.

2. The drug delivery device of claim 1 wherein said carrier is saturated with said drug and wherein an excess of said drug in a solid state is disposed in contact with said drug-saturated carrier.

3. The drug delivery device of claim 1 wherein said membrane is initially hydrated to such an extent that it is structurally manipulable.

4. The drug delivery device of claim 1 wherein said membrane comprises a crosslinked HEMA homopolymer.

5. The drug delivery device of claim 1, which is a monolithic reservoir.

6. The drug delivery device of claim 1 wherein said carrier is silicone oil.

7. A device for the delayed/sustained release of a compound, said device comprising:
    (a) a macromolecular compound having a molecular weight greater than about 1,000;
    (b) a carrier having said macromolecular compound mixed therewith; and
    (c) an initially partially-hydrated, non-biodegradable, hydrogel rate-limiting membrane, wherein said membrane:
        (i) comprises a homopolymer or a copolymer material surrounding said carrier and macromolecular compound,
        (ii) is substantially non-permeable to said macromolecular compound when in said initially partially-hydrated state, and
        (iii) is hydratable, when placed in a delivery environment, to become permeable to said macromolecular compound.

8. The drug delivery device of claim 1 useful as an ocular insert.

9. The drug delivery device of claim 1 wherein said membrane is selected from the group of crosslinked and non-crosslinked homopolymers or copolymers consisting of: HEMA, GMA, HEMA/GMA, HEMA/MMA, GMA/MMA, and HEMA/GMA/MMA.

10. The drug delivery device of claim 9, which is a reservoir, wherein said carrier is silicone oil.

11. The drug delivery device of claim 9 useful as an ocular insert.

12. The drug delivery device of claim 1 wherein said macromolecular drug comprises a hydrophilic polypeptide.

13. The drug delivery device of claim 1 wherein said macromolecular drug comprises a luteinizing hormone-releasing hormone analog or a pharmaceutically acceptable salt thereof.

14. The drug delivery device of claim 13 wherein said carrier is saturated with said drug and wherein an excess of said drug in a solid state is disposed in contact with said drug-saturated carrier.

15. The drug delivery device of claim 13 wherein said analog is a luteinizing hormone-releasing hormone agonist or a pharmaceutically acceptable salt thereof.

16. The drug delivery device of claim 13 wherein said analog is a luteinizing hormone-releasing hormone antagonist or a pharmaceutically acceptable salt thereof.

17. The drug delivery device of claim 13 wherein said analog is nafarelin acetate.

18. The drug delivery device of claim 17 wherein said membrane is initially hydrated to a water content of less than about 30%.

19. The drug delivery device of claim 17 wherein said membrane is hydratable to an equilibrium water content of about 35%–45%.

20. The drug delivery device of claim 17 wherein said membrane is hydratable to an equilibrium water content of about 39%.

21. The drug delivery device of claim 13 wherein said analog is aza-Gly$^{10}$ nafarelin acetate.

22. The drug delivery device of claim 1 wherein said membrane is hydratable to an equilibrium water content such that it limits the diffusion of said macromolecular drug from said carrier to a delivery environment.

23. The drug delivery device of claim 1 wherein said macromolecular drug is selected from the group consisting of: hormonally active polypeptides, mammalian growth hormones, mammalian growth hormone-releasing hormones, and polypeptides having thymosin activity.

24. A pharmaceutical formulation for controlled release of a luteinizing hormone-releasing hormone analog, said formulation comprising:
(a) a pharmaceutically acceptable carrier;
(b) an effective amount of at least one luteinizing hormone-releasing hormone analog or a pharmaceutically acceptable salt thereof disposed in contact with said carrier; and
(c) an initially partially-hydrated, non-biodegradable, hydrogel rate-limiting membrane surrounding said carrier, said membrane being:
(i) initially hydrated to a water content of about 5% to less than about 30% by weight before placement in a delivery environment, and
(ii) hydratable to an equilibrium water content of about 30% to about 80% by weight when in a delivery environment.

25. The formulation of claim 24 wherein said analog is a luteinizing hormone-releasing hormone agonist.

26. The formulation of claim 24 wherein said analog is a luteinizing hormone-releasing hormone antagonist.

27. The formulation of claim 24 wherein said analog is nafarelin acetate.

28. The formulation of claim 25 wherein said analog is a nonapeptide or a decapeptide having the formula:

(pyro)Glu-His-V-Ser-W-X-Y-Arg-Pro-Z or a pharmaceutically acceptable salt thereof, wherein:
V is tryptophyl, phenylalanyl or 3-(1-naphthyl)-L-alanyl;
W is tyrosyl, phenylalanyl or 3-(1-pentafluorophenyl)-L-alanyl;
X is a D-amino acid residue having the formula:

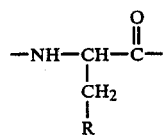

wherein R is:
(a) a carbocyclic aryl-containing radical selected from the group consisting of naphthyl, anthryl, fluorenyl, phenanthryl, biphenylyl, benzhydryl and phenyl substituted with three or more straight chain lower alkyl groups; or
(b) a saturated carbocyclic radical selected from the group consisting of cyclohexyl substituted with three or more straight chain lower alkyl groups, perhydronaphthyl, perhydrobiphenylyl, perhydro-2,2-diphenylmethyl and adamantyl;

Y is leucyl, isoluecyl, nor-leucyl or N-methyl-leucyl; and
Z is glycinamide or —NH—R$_1$,
wherein R$_1$ is lower alkyl, cycloalkyl, fluoro lower alkyl or has the formula:

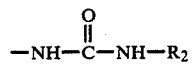

wherein R$_2$ is hydrogen or lower alkyl.

29. The formulation of claim 28 wherein:
V is tryptophyl or phenylalanyl;
W is tyrosyl;
X is 3-(2-naphthyl)-D-alanyl or 3-(2,3,6-trimethylphenyl)-D-alanyl;
I is leucyl or N-methyl-leucyl; and
Z is glycinamide, NHEt or has the formula:

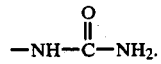

30. The formulation of claim 24 wherein said luteinizing hormone-releasing hormone analog is (pyro)Glu-His-Trp-Ser-Tyr-3-(naphthyl)-D-alanyl-Leu-Arg-Pro-Gly-NH$_2$ or a pharmaceutically acceptable salt thereof.

31. The formulation of claim 30 comprising an ocular insert containing 2.0 mg of said luteinizing hormone-releasing hormone analog suspended in 0.2 ml of a silicone oil carrier, wherein said membrane is a 0.5% EGDMA-crosslinked HEMA homopolymer having an initial water content less than or equal to 29%.

32. The formulation of claim 24 wherein said luteinizing hormone-releasing hormone analog is (pyro)Glu-His-Trp-Ser-Tyr-3-(naphthyl)-D-alanyl-Leu-Arg-Pro-aza-Gly-NH$_2$ or a pharmaceutically acceptable salt thereof.

33. The formulation of claim 32 comprising a reservoir device containing 30.0 mg of said luteinizing hormone-releasing hormone analog suspended in 0.3 ml of a silicone oil carrier, wherein said membrane is a 0.5% EGDMA-crosslinked HEMA homopolymer having an initial water content less than or equal to 29%.

34. The formulation of claim 24, wherein the luteinizing hormone-releasing hormone is an analog of natural luteinizing hormone-releasing hormone, in which the 6-position residue is changed from Gly to a D-amino acid.

35. A formulation according to claim 34, wherein the D-amino acid is D-Ala, D-Lue, D-Phe or D-Trp.

36. A formulation according to claim 34, wherein the D amino acid is D-Leu.

37. A formulation according to claim 34, wherein the D amino acid is D-Trp.

38. The formulation according to claim 24, wherein said carrier is selected from the group:
(a) aqueous systems;
(b) solvents;
(c) solid substrates;
(d) unpolymerized monomers or comonomers;
(e) xerogels;
(f) partially hydrated hydrogels; and
(g) fully hydrated hydrogels.

39. The formulation according to claim 38, wherein said carrier is silicone oil.

40. A drug delivery device for the controlled administration of a macromolecular drug, said device comprising:
(a) a pharmaceutically acceptable carrier;
(b) a macromolecular drug having a molecular weight greater than about 1,000 disposed in contact with said carrier; and
(c) an initially partially-hydrated, non-biodegradable, hydrogel rate-limiting membrane, wherein said membrane:
(i) comprises a homopolymer or a copolymer material surrounding said carrier, and
(ii) has an initial water content such that it is structurally manipulable.

41. The drug delivery device of claim 40 wherein said macromolecular drug is selected from the group consisting of: hormonally active polypeptides, mammalian growth hormones, mammalian growth hormone-releasing hormones, and polypeptides having thymosin activity.

42. The formulation of claim 24 wherein said hydrogel comprises a copolymer of:
(a) 50-100 mole % HEMA;
(b) 0-50 mole % MMA;
(c) 0-10 mole % crosslinking agent; and
(d) 0.01-5 mole % polymerization initiator.

43. The formulation of claim 24 wherein said hydrogel comprises a copolymer of:
(a) 75-100 mole % HEMA;
(b) 0-25 mole % MMA;
(c) 0-5 mole % crosslinking agent; and
(d) 0.01-2 mole % polymerization initiator.

44. The formulation of claim 24 wherein said membrane is selected from the group of crosslinked and non-crosslinked homopolymers or copolymers consisting of: HEMA, GMA, HEMA/GMA, HEMA/MMA, GMA/MMA, and HEMA/GMA/MMA.

45. The formulation according to claim 24, wherein said membrane comprises a 0.32% EGDMA-crosslinked homopolymer of HEMA.

46. The formulation according to claim 24, which is a reservoir device.

47. The formulation according to claim 24 useful as an ocular insert.

48. The device of claim 7 wherein said membrane is hydratable to an equilibrium water content at which it limits the diffusion of said macromolecular compound from said carrier to a delivery environment.

* * * * *